US011052067B2

(12) United States Patent
Bodor et al.

(10) Patent No.: US 11,052,067 B2
(45) Date of Patent: *Jul. 6, 2021

(54) FORMULATION FOR SOFT ANTICHOLINERGIC ANALOGS

(71) Applicant: BODOR LABORATORIES, INC., Miami, FL (US)

(72) Inventors: Nicholas S. Bodor, Bal Harbour, FL (US); John J. Koleng, Austin, TX (US); David Angulo, Tampa, FL (US)

(73) Assignee: Bodor Laboratories, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/107,908

(22) Filed: Nov. 30, 2020

(65) Prior Publication Data
US 2021/0077459 A1 Mar. 18, 2021

Related U.S. Application Data

(63) Continuation of application No. 16/704,659, filed on Dec. 5, 2019, which is a continuation of application No. 15/656,273, filed on Jul. 21, 2017, now abandoned.

(60) Provisional application No. 62/365,037, filed on Jul. 21, 2016.

(51) Int. Cl.
A61K 31/40 (2006.01)
A61K 9/00 (2006.01)
A61K 9/06 (2006.01)
A61K 47/10 (2017.01)
A61K 47/12 (2006.01)
A61K 47/14 (2017.01)
A61K 47/34 (2017.01)
A61K 47/38 (2006.01)

(52) U.S. Cl.
CPC ............ A61K 31/40 (2013.01); A61K 9/0014 (2013.01); A61K 9/06 (2013.01); A61K 47/10 (2013.01); A61K 47/12 (2013.01); A61K 47/14 (2013.01); A61K 47/34 (2013.01); A61K 47/38 (2013.01)

(58) Field of Classification Search
CPC .......... A61Q 15/00; A61K 9/06; A61K 47/10; A61K 9/0014; A61P 17/00
See application file for complete search history.

(56) References Cited

U.S. PATENT DOCUMENTS

| 5,232,689 | A  | 8/1993  | Katsoulis et al. |
| 6,433,003 | B1 | 8/2002  | Bobrove et al. |
| 7,399,861 | B2 | 7/2008  | Bodor |
| 7,417,147 | B2 | 8/2008  | Bodor |
| 7,538,219 | B2 | 5/2009  | Bodor |
| 7,576,210 | B2 | 8/2009  | Bodor |
| 8,071,639 | B2 | 12/2011 | Bodor |
| 8,147,809 | B2 | 4/2012  | Bodor |
| 8,568,699 | B2 | 10/2013 | Bodor |
| 8,628,759 | B2 | 1/2014  | Bodor |
| 9,220,707 | B2 | 12/2015 | Bodor et al. |
| 2003/0064040 | A1 | 4/2003 | Lukacsko |
| 2006/0088496 | A1 | 4/2006 | McManus et al. |
| 2007/0123557 | A1 | 5/2007 | Bodor |
| 2008/0234239 | A1 | 8/2008 | Wheeler et al. |
| 2009/0208437 | A1 | 8/2009 | Woehrmann et al. |
| 2014/0151255 | A1 | 6/2014 | Johnston et al. |
| 2014/0275204 | A1 | 9/2014 | Bodor et al. |
| 2015/0320722 | A1 | 11/2015 | Bodor et al. |
| 2015/0374621 | A1 | 12/2015 | Bodor |

FOREIGN PATENT DOCUMENTS

| CA | 2057081 A1 | 6/1992 |
| CN | 101048126 A | 10/2007 |
| JP | 04-266813 A | 9/1992 |
| JP | 2001-523700 A | 11/2001 |
| JP | 2007/058971 A | 5/2007 |
| JP | 2008-163010 A | 7/2008 |
| JP | 2009-515889 A | 4/2009 |
| JP | 2008-517882 A | 9/2015 |
| JP | 2016-517431 A | 6/2016 |
| JP | 2016-525569 A | 8/2016 |
| JP | 2017-507970 A | 3/2017 |
| WO | 99/26598 A1 | 6/1999 |
| WO | 2014/144075 A8 | 9/2014 |
| WO | 2015/015446 A | 2/2015 |
| WO | 2015/138776 A1 | 9/2015 |
| WO | 2017/015485 A1 | 1/2017 |

OTHER PUBLICATIONS

Examination Report in European Patent Office in Application No. 17831882.0, dated Nov. 23, 2020.
Lachenmeier, Dirk W., "Safety evaluation of topical applications of ethanol on the skin and inside the oral cavity", Journal of Occupational Medicine and Toxicology, vol. 3, No. 26, 16 pages (Nov. 13, 2008).
International Search Report dated Oct. 18, 2017, issued in corresponding International Application No. PCT/US17/43106, 3 pages.
Written Opinion of the International Searching Authority dated Oct. 18, 2017, issued in corresponding International Application No. PCT/US17/43106, 4 pages.
International Search Report and Written Opinion of the International Searching Authority dated Oct. 13, 2016, issued in corresponding International Application No. PCT/US2016/043380, 7 pages.

(Continued)

Primary Examiner — James W Rogers
(74) Attorney, Agent, or Firm — Dentons US LLP

(57) ABSTRACT

Topical formulations comprising soft glycopyrrolates are useful for treating excessive sweating conditions in subjects, such as humans suffering from hyperhidrosis. Preferably, at least one soft anticholinergic agent is provided in an effective amount or concentration in an anhydrous formulation that can inhibit excessive perspiration resulting from a condition such as hyperhidrosis.

29 Claims, No Drawings

(56) References Cited

OTHER PUBLICATIONS

Kirk et al., "Esterification and Esters, Organic", Kirk-Othmer Encyclopedia of Chemical Technology, 4th ed., Feb. 1994, vol. 9, pp. 1-37. ISBN-10 0471526770. http://vigoschools.org/-mmc3/AP%20Lab/ap%/20lab%20documents/Esterification.pdf.

Sakamuri, Raj, "Esters, Organic", Kirk-Othmer Encyclopedia of Chemical Technology, John Wiley & Sons, Inc., Dec. 19, 2003, pp. 497-526.

Extended European Search Report dated Feb. 20, 2019 issued in corresponding European Application No. 16828553.4, 9 pages.

Abrutyn, Eric S., "Deciphering Antiperspirant Formulas", Cosmetics & Toiletries—Science Applied, Nov. 11, 2013, 11 pages.

Written Opinion dated Jan. 31, 2019, issued in corresponding Singapore Patent Application No. 11201800526Q, 8 pages.

European Office Action dated Oct. 6, 2017 in corresponding European Patent Application No. 15762178.0, 8 pages.

Japanese Office Action dated Oct. 4, 2017 in corresponding Japanese Patent Application No. 2016-556899, 7 pages.

Chinese Office Action dated Aug. 2, 2018 in corresponding Chinese Patent Application No. 201580013622.0, 21 pages.

Japanese Office Action dated Aug. 16, 2019 in corresponding Japanese Patent Application No. 2018-502683 and English translation, 13 pages.

Raj Sakamuri, "Esters, Organic", Kirk-Othmer Encyclopedia of Chemical Technology, John Wiley & Sons, Inc., vol. 10, pp. 497-526 (Dec. 19, 2003).

Aoyagi, Takao, "Study on transdermal absorption enhancer regarding safety of skin", Fragrance Journal, Apr. 15, 1996, vol. 24, No. 4, pp. 34-41.

Taylor, A. K., "Isopropyl Myristate", Handbook of Pharmaceutical Excipients Fifth Edition, Feb. 28, 2007, pp. 953-955.

European Search Report dated Feb. 5, 2020 in corresponding European Patent Application No. 17831882.0, 14 pages.

Taiwanese Office Action dated May 8, 2020 in corresponding Taiwan Patent Application No. 105128352 and English translation, 10 pages.

Office Action of Chinese Patent Office in Application No. 201680054285.4, dated Jan. 5, 2021.

Yan, Yaodong, "Design and Development of Sustained-release and Controlled-release Preparations", Chinese Medical Science and Technology Publishing House, Jun. 30, 2006, p. 426.

FORMULATION FOR SOFT ANTICHOLINERGIC ANALOGS

CROSS-REFERENCE TO EARLIER APPLICATIONS

This application is a Continuation of U.S. patent application Ser. No. 16/704,659, filed Dec. 5, 2019, now allowed, which is a Continuation of Ser. No. 15/656,273, filed Jul. 21, 2017, now abandoned, which claims benefit of U.S. Provisional Patent Application No. 62/365,037, filed Jul. 21, 2016, all of which are hereby incorporated by reference in their entirety for all purposes as if fully set forth herein.

BACKGROUND

Various anticholinergic compounds and formulations for those compounds have been previously described. Muscarinic receptor antagonists are frequently used therapeutic agents that inhibit the effects of acetylcholine by blocking its binding to muscarinic cholinergic receptors at neuroeffector sites on smooth muscle, cardiac muscle, and gland cells as well as in peripheral ganglia and in the central nervous system (CNS). However, their side effects, which can include dry mouth, photophobia, blurred vision, urinary hesitancy and retention, drowsiness, dizziness, restlessness, irritability, disorientation, hallucinations, tachycardia and cardiac arrhythmias, nausea, constipation, and severe allergic reactions, often limit their clinical use. Topical administration of anticholinergic agents to targeted areas, such as sweat glands, where the localized blockage of muscarinic receptors will be of clinical benefit, would be a desirable therapeutic strategy. However, currently used topical anticholinergics can exhibit unwanted systemic side effects which can limit the dosage that can be safely administered.

Glycopyrrolate is among the quaternary ammonium anticholinergics which have reduced CNS-related side effects as they cannot cross the blood-brain barrier; however, because glycopyrrolate is eliminated mainly as unchanged drug or active metabolite, its topical administration is often associated with common undesirable anticholinergic systemic side effects. To increase the therapeutic index of anticholinergics, the soft drug approach has been applied in a number of different designs starting from various lead compounds, but there is a need for yet other new soft anticholinergics with clinically meaningful biological activity. These novel muscarinic antagonists, just as all other soft drugs, are designed to elicit their intended pharmacological effect at the site of application, but to be quickly metabolized into their designed-in, inactive metabolite upon entering the systemic circulation and rapidly eliminated from the body, resulting in reduced systemic side effects and an increased therapeutic index.

Soft anticholinergic zwitterions have been described in US Patent Publication No. 2012/0141401 (now U.S. Pat. No. 8,568,699), and its related patents, U.S. Pat. Nos. 8,071,693; 7,538,219; and 7,417,147. Soft anticholinergic esters have been described in US Patent Publication No. 2012/0177590 (now U.S. Pat. No. 8,628,759) and its related patents U.S. Pat. Nos. 8,147,809; 7,576,210; and 7,399,861. Although these published applications and patents identified the potential for the zwitterion or ester forms of anticholinergics to be used for treating hyperhidrosis, the fact that activity and duration of action against hyperhidrosis are unexpectedly high herein, based on a comparison to published mydriasis data, was not known or previously described.

Each of the US Patent Publication Nos. 2012/0141401 (U.S. Pat. No. 8,568,699) and 2012/0177590 (U.S. Pat. No. 8,628,759), and their related patents U.S. Pat. Nos. 8,147,809; 8,071,693; 7,576,210; 7,538,219; 7,417,147; and 7,399,861 are hereby incorporated by reference in their entireties.

Hyperhidrosis is an idiopathic pathological condition characterized by excessive, uncontrollable sweating beyond that required to cool the body. A hyperfunction of the sweat glands and a disturbance of their cholinergic stimulation have been described as possible causes of this condition. It is known to affect approximately 3% of the population. Hyperhidrosis not only may result in intense social embarrassment, but also may even interfere with a person's occupation.

Hyperhidrosis most often involves one or several areas, especially the hands, axillae, feet or face, although it can even involve the whole body. Axillary hyperhidrosis is the most common form, followed by palmar hyperhidrosis. Antiperspirants alone are generally not effective in treating this excessive perspiration. Oral medications are occasionally beneficial, but may have side effects. Other therapeutic alternatives include surgical procedure such as endoscopic thoracic sympathectomy. Although the surgery affords permanent benefit in some 40% to 90% of affected individuals, it is invasive, requires general anesthesia and is not without potential side effects. As many as 50% of persons who have undergone thoracic sympathectomy develop compensatory and annoying sweating of the trunk or thighs. Botulinum A neurotoxin (BOTOX), which blocks the action on sweat glands of acetylcholine that is released by the autonomic nerves, has proven effective in hyperhidrosis. Minute amounts of BOTOX injected into the palms or axillae of affected individuals result in statistically significant benefit. The effect lasts for several months but requires repeated injections and is often not a suitable alternative for pediatric patients. Iontophoresis has limited efficacy and cannot be used for axillary areas.

A non-invasive, convenient and effective treatment having high sweat reduction activity, long duration and with fewer side effects would be a welcome alternative for treating hyperhidrosis. An improved method of treating hyperhidrosis has recently been described in copending U.S. patent application Ser. No. 14/213,242, filed Mar. 14, 2014 (inventors BODOR and ANGULO), incorporated by reference herein in its entirety.

Topical formulations comprising soft anticholinergic analogs, such as soft ester analogs of glycopyrrolate, have been previously proposed for use in treating hyperhidrosis; however, stable, pharmaceutically acceptable formulations of such esters which can meet regulatory requirements or provide commercially viable shelf-life for such products have been elusive. Thus, what is needed in the art is a stable, pharmaceutically acceptable, and commercially viable formulation for a topically administered composition comprising a soft anticholinergic analog.

SUMMARY

The subject application concerns topical formulations for treating excessive sweating conditions in subjects, such as humans suffering from hyperhidrosis. A composition herein comprises at least one soft anticholinergic agent, which is a soft ester analog of glycopyrrolate, in an effective amount or concentration that can inhibit excessive perspiration resulting from a condition such as hyperhidrosis. One embodiment is a topical composition comprising: (a) at least one compound having the formula (1):

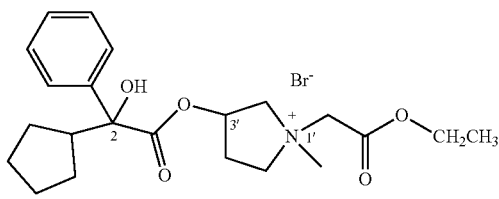

(1)

said compound having the R, S, or RS stereoisomeric configuration at the 2 position and 1' and 3' positions, or being a mixture thereof, and (b) anhydrous ethanol, provided that said topical composition is anhydrous.

One preferred embodiment of a topical composition comprises: (a) at least one compound having the following stereospecific formula (2):

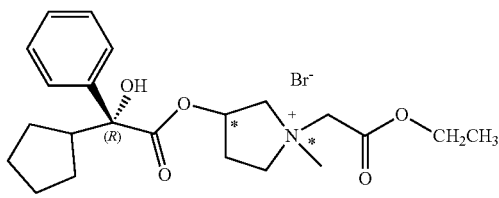

(2)

said compound having the R stereoisomeric configuration at the 2 position and having the R, S, or RS stereoisomeric configuration at the 1' and 3' positions (designated by asterisks), or being a mixture thereof, and (b) anhydrous ethanol, provided that said topical composition is anhydrous.

Another embodiment provides a topical pharmaceutical composition comprising (a) one or more compounds of the foregoing formula (2), (b) anhydrous ethanol and (c) one or more pharmaceutically acceptable carriers or excipients, provided that said topical composition is anhydrous. Yet another embodiment provides a topical composition comprising (a) and (b) above; (c) optionally, at least one gelling or viscosity controlling ingredient; and (d) optionally at least one additional carrier or excipient; provided that said topical composition is anhydrous and comprises from about 1% to about 25% of the compound of formula (2), said composition having greater storage stability compared to a composition comprising an aqueous solvent or aqueous buffer.

Methods of treating or inhibiting or ameliorating excessive sweating, including conditions such as hyperhidrosis, using a topical composition as described herein, are also included. The methods of copending U.S. patent application Ser. No. 14/213,242, filed Mar. 14, 2014, are of particular interest and advantage when carried out by administering a topical formulation comprising an ethyl ester of formula (2) above and anhydrous ethanol, provided that said topical formulation is anhydrous.

A composition of the subject application can be formulated as a solid or semi-solid, powder, gel, cream, lotion, foam, solution, suspension, aerosol, patch, wipes or emulsion, or the like, and is formulated for topical application for the treatment, inhibition or amelioration of hyperhidrosis. More preferably, a composition as defined above is formulated as an anhydrous ethanol topical gel, which can provide certain advantages, including superior stability or increased shelf-life for the composition, as well as the benefit of minimizing or eliminating the need for a separate preservative in the composition.

Additional advantages for a topical anhydrous ethanol gel composition herein include properties such as fast drying time, limited residue on the skin or clothing, and facilitation of a capability to be dispensed in metered amounts of product per application. A particular formulation can further mask stickiness properties that some soft anticholinergics, such as certain compounds described herein, may have.

One formulation comprises about 0.1% to about 30% of the compound in 70-99.9% of the non-aqueous solvent, ethanol. The formulation can further include one or more additional carriers or excipients, including a gelling or viscosity controlling excipient, which itself is anhydrous, that is non-aqueous.

The compounds of formulas (1) and (2) are ethyl esters. As esters, these compounds are subject to transesterification, which is the process of exchanging the alkyl group of the ester with the alkyl group of an alcohol/alkanol. This reaction is catalyzed by acid or base or even enzymatically. Unfortunately, transesterification can lead to an interchange of a significant amount of the drug's ester group for a less desirable, less biologically acceptable group. For example, use of anhydrous methanol as solvent for the ethyl ester leads to unacceptable formation of a significant amount of methyl ester mixed with ethyl ester. Use of anhydrous ethanol, on the other hand, leads only to formation of ethyl ester as a product of transesterification. Further, by using anhydrous ethanol, and by making certain that the composition itself is anhydrous, it is possible to avoid hydrolysis of the active ingredient's ethyl ester group.

There is thus provided in one aspect herein a method for treating, inhibiting or ameliorating hyperhidrosis in a subject which comprises:

(A) providing a topical composition comprising: (a) from about 1% to about 25% of a compound having the formula (1):

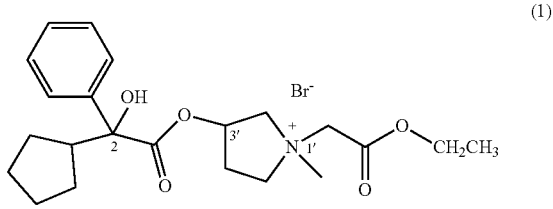

(1)

said compound having the R, S or RS stereoisomeric configuration at the 2 position and 1' and 3' positions, or being a mixture thereof; (b) anhydrous ethanol; (c) optionally, at least one gelling or viscosity-controlling ingredient; and (d) optionally, at least one additional carrier or excipient; provided that said topical composition is anhydrous; and (B) topically administering the composition to a subject suffering from excessive sweating, such as hyperhidrosis.

There is further provided in another aspect herein a method for treating, inhibiting or ameliorating hyperhidrosis in a subject which comprises:

(A) providing a topical composition comprising: (a) from about 1% to about 25% of a compound having the formula (2):

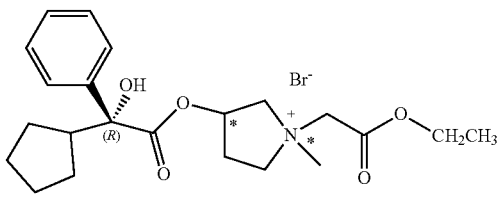

(2)

said compound having the R stereoisomeric configuration at the 2 position and the R, S, or RS stereoisomeric configuration at the 1' and 3' positions, or being a mixture thereof, (b) anhydrous ethanol; (c) optionally, at least one gelling or viscosity-controlling ingredient; and (d) optionally, at least one additional carrier or excipient; provided that said topical composition is anhydrous; and (B) topically administering the composition to a subject suffering from excessive sweating, such as hyperhidrosis.

Advantageously, the method can provide reduction of excessive sweating for up to about 48 hours. Moreover, surprisingly, topical administration of the composition can unexpectedly provide a reduction in sweat production, as compared to baseline conditions, for at least about six (6) hours by an amount which is substantially equivalent to the reduction of sweat production resulting from administration of a composition comprising an equivalent concentration of glycopyrrolate, also compared to baseline conditions. Soft ester analogs of glycopyrrolate were previously believed to require up to 5-10 times the concentration of glycopyrrolate to provide substantially equivalent activity.

A preferred method of treating hyperhidrosis in a subject in need of same or for treating, inhibiting or ameliorating excessive sweating therein, comprises administering the instant composition in accord with the methods of U.S. patent application Ser. No. 14/213,242. In accord therewith, the composition as defined herein comprising a compound of formula (2) above is administered to skin of a subject suffering from hyperhidrosis, before bedtime, such that, compared to untreated, baseline conditions, sweat production is reduced by at least 25% for at least six (6) hours; and such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate. In particular, at 5% drug concentration, no systemic anticholinergic side effects were observed for the soft ester in testing described in the '242 application. Also, no systemic anticholinergic side effects were observed in clinical studies at 5% or 10% as described hereinbelow.

The present method is preferably carried out by topically administering the composition to a human subject, to the skin of the subject at a superficial anatomic area in need of sweat reduction. Preferably, the anatomic area for application or administration of the composition is selected from a hand palm area, a foot plantar area, a groin area, an axilla area, and a facial area of the subject.

The subject method can reduce sweat production by about 25% to about 99%, preferably by about 30% to about 90%, more preferably by at least 50%, which can be a clinically significant endpoint for an indication for treating hyperhidrosis.

As previously described, the method can employ the composition formulated as a solid or semisolid, powder, gel, cream, lotion, foam, solution, suspension, aerosol, patch, wipes or emulsion, or the like and can comprise from about 0.1% to about 30% concentration of the compound, preferably from about 1% to about 25% concentration of the compound, more preferably about 1% to about 20% concentration of the compound, and most preferably about 2% to about 10% concentration of the compound of formula (1) above, preferably of formula (2).

A method in accordance with the present description can comprise topically administering to a subject as needed (prn), a composition as defined herein. Administrations are preferably at least one time per week, more preferably at least three to four times per week (e.g., every other day), or can be administered more frequently such as once daily (QD), for example, before bedtime (typically, at night) or after the subject awakens (typically in the morning, and preferably after a bath or shower); twice daily (BID), e.g., every 10-12 hours; thrice daily (TID), e.g., every 6-9 hours; four times daily (QID), e.g., every 3-5 hours; with a preferred upper limit of about 6-8 doses or applications per day.

Surprisingly, the subject method, after single or multiple applications, can reduce sweat production for a period of from about 4 hours to about 24 hours, and preferably for a period of from about 6 hours to about 12 hours.

A preferred composition herein comprises:
one or more soft glycopyrrolate analogs of formula (1) or (2) as active ingredient; and
anhydrous ethanol (as non-aqueous solvent for the active ingredient);
provided that said composition is anhydrous.

As described herein, the subject formulation is preferably a gel. Accordingly a more preferred composition comprises:
one or more soft glycopyrrolate analogs of formula (1) or (2) as active ingredient; anhydrous ethanol (as non-aqueous, pharmaceutically acceptable solvent for the active ingredient); and
one or more gelling or viscosity-controlling agents,
provided that said formulation is anhydrous.

The soft glycopyrrolate analog of formula (1) or (2) is a soft anticholinergic ethyl ester. The use of the matching non-aqueous solvent ethanol avoids mixtures of esters which can result from transesterification when an alcohol such as methanol is used as solvent for the ethyl ester. Moreover, the absence of water results in much greater storage stability.

Advantageously, anhydrous ethanol can provide for a self-preserving composition, which can provide microbial stability to the composition without added preservatives.

Anhydrous ethanol can also inhibit bacterial growth and provide deodorant properties to the composition.

A further advantage of a composition according to the present description is provided by the fact that the non-aqueous solvent, anhydrous ethanol, is volatile, especially at localized temperatures generated by body heat so that, when it is topically applied to a subject, it provides a rapidly drying composition.

A preferred gelling or viscosity controlling agent can be a modified cellulose, e.g., hydroxypropyl cellulose (HPC), such as the commercially available KLUCEL™, which can preferably provide viscosity of the composition of from about 100 to about 10,000 cps.

DETAILED DESCRIPTION

Throughout this specification, the following definitions, general statements and illustrations are applicable.

The patents, published applications and scientific literature referred to herein establish the knowledge of those with skill in the art and are hereby incorporated by reference in their entireties to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used herein, whether in a transitional phrase or in the body of a claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a composition, the term "comprising" means that the composition includes at least the recited features or components, but may also include additional features or components.

The terms "consists essentially of" or "consisting essentially of" have a partially closed meaning, that is, they do not permit inclusion of steps or features or components which would substantially change the essential characteristics of a process or composition; for example, steps or features or components which would significantly interfere with the desired properties of the compounds or compositions described herein, i.e., the process or composition is limited to the specified steps or materials and those which do not materially affect the basic and novel characteristics of the process or composition.

The terms "consists of" and "consists" are closed terminology and allow only for the inclusion of the recited steps or features or components.

As used herein, the singular forms "a," "an" and "the" specifically also encompass the plural forms of the terms to which they refer, unless the content clearly dictates otherwise.

The term "about" is used herein to mean approximately, in the region of, roughly, or around. When the term "about" is used in conjunction with a numerical range, it modifies that range by extending the boundaries above and below the numerical values set forth. In general, the term "about" or "approximately" is used herein to modify a numerical value above and below the stated value by a variance of 20%.

As used herein, the recitation of a numerical range for a variable is intended to convey that the variable can be equal to any values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

In the specification and claims, the singular forms include plural referents unless the context clearly dictates otherwise. As used herein, unless specifically indicated otherwise, the word "or" is used in the "inclusive" sense of "and/or" and not the "exclusive" sense of "either/or."

Technical and scientific terms used herein have the meaning commonly understood by one of skill in the art to which the present description pertains, unless otherwise defined. Reference is made herein to various methodologies and materials known to those of skill in the art. Standard reference works setting forth the general principles of pharmacology include Goodman and Gilman's The Pharmacological Basis of Therapeutics, 10th Ed., McGraw Hill Companies Inc., New York (2001).

As used herein, "treating" means reducing, hindering or inhibiting the development of, controlling, inhibiting, alleviating and/or reversing the symptoms in the individual to which a composition comprising a compound of formula (1) or (2) has been administered, as compared to the symptoms of an individual not being administered the compound or composition. A practitioner will appreciate that the combinations, compositions, dosage forms and methods described herein are to be used in concomitance with continuous clinical evaluations by a skilled practitioner (physician or veterinarian) to determine subsequent therapy. Such evaluation will aid and inform in evaluating whether to increase, reduce or continue a particular treatment dose, and/or to alter the mode of administration.

The subject compounds or compositions can also prevent the symptoms, or prevent the occurrence of the symptoms, in the individual to which a composition comprising a compound of formula (1) or (2) above has been administered, as compared to the symptoms of an individual not being administered the compound or composition. This is not a prevention of hyperhidrosis or excessive sweating in the absolute sense, it does not prevent the medical condition, as it does not even address the condition's cause; rather it inhibits the manifestation of the condition for the period of time (hours) for which the administered dose is effective.

The methods described herein are intended for use with any subject/patient that may experience their benefits. Thus, the terms "subjects" as well as "patients," "individuals" and "warm-blooded animals" include humans as well as non-human subjects, such as animals that may experience excessive sweating.

Compounds useful in a composition herein include those of the formula (1):

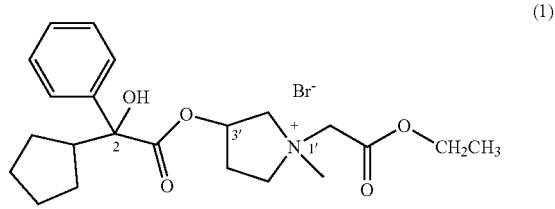

The compound has the R, S, or RS stereoisomeric configuration at the 2 position and at the 1' and 3' positions, or is a mixture thereof.

Compounds having the R configuration with respect to chiral center 2 are of particular interest for use in the instant compositions. For example, a preferred compound useful in a composition herein has the stereospecific formula (2):

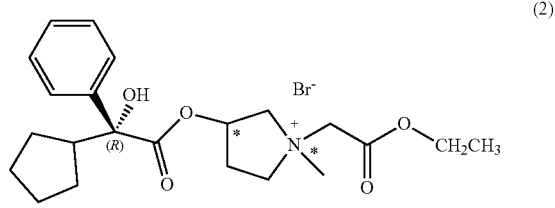

said compound having the R stereoisomeric configuration at the 2 position and the R, S, or RS stereoisomeric configuration at the 1' and 3' positions (designated by asterisks), or being a mixture thereof.

The following compounds are of particular interest for use in a composition of the present description:
(i) 3-(2-cyclopentylphenylhydroxyacetoxy)-1'-methyl-1'-ethoxycarbonylmethylpyrrolidinium bromide;
(ii) 3-[2(R)-cyclopentylphenylhydroxyacetoxy]-1'-methyl-1'-ethoxycarbonylmethylpyrrolidinium bromide;
(iii) 3'(R)-[2(R)-cyclopentylphenylhydroxyacetoxy]-1'-methyl-1'-ethoxycarbonylmethylpyrrolidinium bromide;
(iv) 3'(S)-[2(R)-cyclopentylphenylhydroxyacetoxy]-1'-methyl-1'-ethoxycarbonylmethylpyrrolidinium bromide;
(v) 1'(R)-3'(S)-[2(R)-cyclopentylphenylhydroxyacetoxy]-1'-methyl-1'-ethoxycarbonylmethylpyrrolidinium bromide;
(vi) 1'(S)-3'(S)-[2(R)-cyclopentylphenylhydroxyacetoxy]-1'-methyl-1'-ethoxycarbonylmethylpyrrolidinium bromide;
(vii) 1'(R)-3'(R)-[2(R)-cyclopentylphenylhydroxyacetoxy]-1'-methyl-1'-ethoxycarbonylmethylpyrrolidinium bromide; and
(viii) 1'(S)-3'(R)-[2(R)-cyclopentylphenylhydroxyacetoxy]-1'-methyl-1'-ethoxycarbonylmethylpyrrolidinium bromide.

It is noted that the above compounds are identical to those originally disclosed with a correct, but different, naming scheme, in U.S. Provisional Patent Application Ser. No. 61/952,505 filed Mar. 13, 2014. The compounds were previously and respectively disclosed as:
(i) 3-(2-cyclopentyl-2-phenyl-2-hydroxyacetoxy)-1-(ethoxycarbonylmethyl)-1-methylpyrrolidinium bromide;
(ii) (2R) 3-(2-cyclopentyl-2-phenyl-2-hydroxyacetoxy)-1-(ethoxycarbonylmethyl)-1-methylpyrrolidinium bromide;
(iii) (2R, 3'R) 3-(2-cyclopentyl-2-phenyl-2-hydroxyacetoxy)-1-(ethoxycarbonylmethyl)-1-methylpyrrolidinium bromide;
(iv) (2R,3'S) 3-(2-cyclopentyl-2-phenyl-2-hydroxyacetoxy)-1-(ethoxycarbonylmethyl)-1-methylpyrrolidinium bromide;
(v) (2R,1'R,3'S) 3-(2-cyclopentyl-2-phenyl-2-hydroxyacetoxy)-1-(ethoxycarbonylmethyl)-1-methylpyrrolidinium bromide;
(vi) (2R,1'S,3'S) 3-(2-cyclopentyl-2-phenyl-2-hydroxyacetoxy)-1-(ethoxycarbonylmethyl)-1-methylpyrrolidinium bromide;
(vii) (2R,1'R,3'R) 3-(2-cyclopentyl-2-phenyl-2-hydroxyacetoxy)-1-(ethoxycarbonylmethyl)-1-methylpyrrolidinium bromide; and
(viii) (2R,1'S,3'R) 3-(2-cyclopentyl-2-phenyl-2-hydroxyacetoxy)-1-(ethoxycarbonylmethyl)-1-methylpyrrolidinium bromide.

The above compounds (i)-(viii) can be used alone or two or more of the above compounds can be used in combination in a single composition. Various methods of making the instant compounds are described in the art.

An anticholinergically effective amount of such an agent inhibits the effect of acetylcholine by blocking its binding to muscarinic cholinergic receptors at neuroeffector sites. Subjects in need of a method of eliciting an anticholinergic response are those suffering from conditions which respond to treatment with an anticholinergic agent, including subjects suffering from excessive sweating or hyperhidrosis.

The compound of formula (1) or (2) is typically administered in the form of a pharmaceutical composition comprising an anticholinergically effective amount of the compound, anhydrous ethanol and a non-toxic pharmaceutically acceptable carrier or excipient, provided that the composition itself is also anhydrous. Pharmaceutically acceptable carriers, or diluents, are well-known in the art. The carriers may be any inert material, organic or inorganic, powders, liquid, or gases suitable for administration, such as: alcohol such as hexylene glycol, gelatin, gum arabic, lactose, microcrystalline cellulose, starch, sodium starch glycolate, calcium hydrogen phosphate, magnesium stearate, talcum, colloidal silicon dioxide, and the like, provided that the ingredients are anhydrous.

It has been discovered that the instant formulations, having advantageous properties, result when no water or aqueous carrier is added to the formulation. Thus, a composition herein is an anhydrous formulation. By the term "anhydrous", is meant the ordinary scientific meaning of the word, that is, that no water or aqueous excipient is added to the formulation.

Such compositions may also contain conventional additives such as solvents, stabilizers, wetting agents, emulsifiers, buffers, binders, disintegrants, fragrances, lubricants, glidants, antiadherents, propellants, and the like, just so long as the additives and compositions are anhydrous, that is, free of water to the extent required to avoid significant negative impact on the storage stability of the composition (by hydrolysis of the ester drug).

The active ingredient is dissolved in anhydrous ethanol as a solvent, in which the compound is soluble or at least slightly soluble. It is preferred that the apparent pH of the composition be acidic (i.e. apparent pH <7).

The composition herein can be formulated as a solid, semi-solid, or liquid, such as in the form of powders, solutions, lotions, creams, gels, semi-solid sticks, foams, sprays, aerosols, solutions, suspensions or emulsions, patches, wipes and the like, and is formulated for topical administration. By way of illustration only, for treating hyperhidrosis, a topical preparation formulated as an anhydrous antiperspirant stick, gel, spray, cream, solution, foam, emulsion or the like can be preferred.

In preparing a formulation, it may be necessary to mill the active compound to provide the appropriate particle size prior to combining with the other ingredients. The active compound can be milled to a particle size of less than 200 mesh.

Some examples of suitable topical carriers or excipients, to be added to the compound of formula (1) or (2) in absolute ethanol, include alcohols such as hexylene glycol and propylene glycol, dimethicone, e.g. dimethicone 350 cSt, dimethicone copolyol, Dimethiconol Blend 20, dimethiconol 20 cSt, cyclomethicone, e.g. cyclomethicone 5-NF, PGE, allantoin, glycerin, vitamin A and E oils, mineral oil, PPG2, myristyl propionate, isopropyl myristate, $C_{12\text{-}15}$ alkyl lactate, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, and methyl cellulose, and mixtures thereof. The formulations can additionally include: lubricating agents such as talc, magnesium stearate, and mineral oil; wetting agents; emulsifying and suspending agents; and preserving agents such as methyl- and propylhydroxy-benzoates. The compositions can be formulated so as to provide quick, modified, sustained or delayed release or activity of the active ingredient after administration and/or application to the subject by employing procedures known in the art. The use of a separate preserving agent can be avoided by judicious selection of other ingredients, as discussed in more detail below.

The composition may additionally contain one or more optional additives such as colorants, perfumes, or the like. In practice, each of these optional additives should be compatible with the active compound. Compatible additives are those that do not prevent the use of or result in the degradation of the compound in the manner described herein.

For purposes of illustration, liquid formulation dosages are expressed based on a percent solution (g/100 ml) or percent concentration (w/v) unless otherwise stated. For solid formulation dosages, the percent concentration can be expressed as mg/mg, or w/w concentrations unless otherwise stated. A person of ordinary skill in the art would readily understand the percent concentration in the context of the type of formulation described.

In general, a therapeutically effective or anticholinergically effective amount of a compound of formula (1) or (2) herein is from an about 1% solution (10 mg/ml) to an about 30% solution (300 mg/ml). Preferably, the topical composition dose is from about 1% concentration to about 25% concentration, or more preferably from about 1% concentration to about 20% concentration, especially from 2% to 10%, and is most preferred using a dose application volume of approximately 0.5 to about 1.0 ml or 2.0 ml of a composition comprising about 3% to about 6%, e.g., about 5%, of the compound per treated area. The exact dosage of a compound in the instant composition can vary depending on its potency, the mode of administration, the application area, the age and weight of the subject and the severity of the condition to be treated. The daily dosage may be administered singly or multiply one to four times daily or more.

Administration prior to bedtime (in accord with a preferred method of treating hyperhidrosis herein) does not imply at night or a particular hour or time of day; rather, before or prior to bedtime means that the composition is preferably administered, generally within about 1-2 hours prior to a person's normal rest or sleep (typically 4 to 10-hour) period. A before bedtime administration time can provide a preferred response or activity of the active compounds of formulas (1) and (2), in accord with the method of prior copending U.S. patent application Ser. No. 14/213,242.

Administration of a composition as described herein can provide a substantially identical or similar clinical (sweat reduction) response in a subject, as compared to administration of a composition containing the same concentration of glycopyrrolate. Thus, the results of this discovery are surprising in view of previously published mydriatic studies which suggested that the subject compounds in a composition were required to be present in concentration from 5 times to 10 times the concentration of a glycopyrrolate composition exhibiting a similar or substantially identical clinical response.

In addition, administration of a second dose within about 6-10 hours following the initial dose can also be a preferred method of administration or dosing regimen.

The topical composition for treating hyperhidrosis can be a liquid solution, semi-solid, or solid. Solutions are prepared in the usual way, e.g. with the addition of excipients as well as the anhydrous ethanol solvent and can include preservatives such as p-hydroxybenzoates, or stabilizers such as alkali metal salts of ethylenediamine tetraacetic acid, optionally using emulsifiers and/or dispersants, and other organic solvents may optionally be used as solvating agents or dissolving aids, and transferred into vials, ampules, bottles, tubes, syringes, or the like.

However, the anhydrous composition can have the advantage of minimizing, or eliminating, the need for an additional preservative to be included in the formulation. Thus, one preferred embodiment of a composition is a substantially "preservative-free" composition. By "preservative-free" is meant that the composition, although containing ethanol and even possibly another organic solvent which may provide some preserving properties, has no additional preservative component, added specifically for its preservative property to the composition.

Additional carriers or excipients may be used in a composition herein, including, for example, pharmaceutically acceptable organic solvents such as paraffins (e.g. petroleum fractions), vegetable oils (e.g. groundnut or sesame oil), mono- or polyfunctional alcohols (e.g. hexylene glycol or glycerol), carriers such as natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulfite liquors, methylcellulose, starch and polyvinylpyrrolidone) and lubricants (e.g. magnesium stearate, talc, stearic acid and sodium lauryl sulphate).

Compositions herein can be formulated using known techniques, and are generally accepted as being formulated with commonly known excipients, including preservatives if needed. For example, the patent literature describes that soft glycopyrrolate compounds are at least partially water-soluble. Accordingly, soft glycopyrrolates compounds, such as soft anticholinergic analogs (e.g., esters) were earlier described as capable of being formulated in buffer (aqueous or water-based) solutions. However, aqueous components added to the formulation increase the hydrolysis products found in the composition, and decrease the stability of the active compound, and consequently decrease the shelf-life of the product compared to anhydrous formulations comprising a soft anticholinergic analog (ester) as an active ingredient.

Moreover, decreased stability and increased hydrolysis products found for a soft anticholinergic analog (ester) formulated in an aqueous or water-based composition would suggest or even require an added preservative to be included in the composition.

In addition to the general preference or need to decrease exposure to preservative chemicals by the subject being treated, certain ingredients, such as the antioxidant/pH adjuster ascorbic acid, can have additional disadvantages when topically applied. For example, an aqueous preparation comprising ascorbic acid was found to produce a pink-colored residue on the skin of individuals after a few to several hours following exposure to the preparation.

A preservative-free composition, which is also an ascorbic acid-free composition, can therefore provide a further advantage of maintaining a colorless preparation following application and during residence on the skin of a subject. A composition comprising citric acid as an antioxidant/pH adjuster did not result in a pink colored residue following application of the composition to the skin; therefore a composition herein can include citric acid as an antioxidant.

Experimental data demonstrate that aqueous or water-based compositions result in the presence of increased hydrolysis products in the composition, and decreased stability of the composition, which leads to reduced shelf-life for a product comprising the composition. Adequate shelf-life is an advantageous factor for regulatory approval, as well as commercial success for a topical gel composition.

The HPLC experimental data presented in EXAMPLE 1 below also demonstrate the reduction of hydrolysis products Identified, and increased stability for a product comprising an anhydrous topical gel in accordance with the subject description.

EXAMPLE 1

Proof of Concept

Aqueous, or water-based, topical formulations are the most common in view of the availability of gel-forming components which interact with water to form hydrogels. The following experiments were conducted using the compound, (2R,3'R) 3-(2-cyclopentyl-2-phenyl-2-hydroxyacetoxy)-1-(ethoxycarbonylmethyl)-1-methylpyrrolidinium bromide, (compound (iii) in the above list), which is designated as "BBI-4000" for convenience of reference.

Various formulations of approximately 2% BBI-4000 were made and their stabilities assessed. The solvent systems were as follows:
(a) solvent content: 100% water;
(b) solvent content: 60% water/40% ethanol;
(c) solvent content: 30% water/70% ethanol;
(d) solvent content: 100% ethanol.
Each sample was assessed at baseline; after 7 days at 25° C./60% humidity; and after 7 days at 40° C./75% humidity. The percentage change from baseline for 40° C. after 7 days was calculated in each case. HPLC analysis was conducted as described in EXAMPLE 2 below.

Testing conclusively showed that, of the four solvent systems tested, only 100% ethanol (i.e. absolute or anhydrous ethanol) was capable of providing a composition which essentially maintained the baseline amount of BBI-4000 even after 7 days at the elevated temperature of 40° C. There is clearly a dramatic difference in the stability of the anhydrous ethanol formulation compared to the water-containing formulations. The results are shown in TABLE I below.

TABLE I

| | Formulation Solvent Content: 100% Water | | | |
|---|---|---|---|---|
| Condition/ Timepoint | Baseline | Day 7 @ 25° C./60% | Day 7 @ 40° C./75% | Change from Baseline (40° C./75%) |
| BBI-4000 Assay | 1.99% | 1.91% | 1.80% | reduction 9.5% |
| BBI-4000 Main Hydrolysis Products (RRT-0.79-0.84) | 0 | 1.90% | 7.42% | |

| | Formulation Solvent Content: 60% water, 40% ethanol | | | |
|---|---|---|---|---|
| Condition/ Timepoint | Baseline | Day 7 @ 25° C./60% | Day 7 @ 40° C./75% | Change from Baseline (40° C./75%) |
| BBI-4000 Assay | 1.99% | 1.94% | 1.89% | reduction 5% |
| BBI-4000 Main Hydrolysis Products (RRT-0.79-0.84) | 0 | 0.83% | 3.40% | |

TABLE I-continued

| | Formulation Solvent Content: 30% water, 70% ethanol | | | |
|---|---|---|---|---|
| Condition/ Timepoint | Baseline | Day 7 @ 25° C./60% | Day 7 @ 40° C./75% | Change from Baseline (40° C./75%) |
| BBI-4000 Assay | 1.99% | 1.95% | 1.89% | reduction 5% |
| BBI-4000 Main Hydrolysis Products (RRT-0.79-0.84) | 0 | 0.84% | 3.50% | |

| | Formulation Solvent Content: 100% Ethanol | | | |
|---|---|---|---|---|
| Condition/ Timepoint | Baseline | Day 7 @ 25° C./60% | Day 7 @ 40° C./75% | Change from Baseline (40° C./75%) |
| BBI-4000 Assay | 2.02% | 2% | 2.01% | reduction <1% |
| BBI-4000 Main Hydrolysis Products (RRT-0.79-0.84) | 0 | 0 | 0 | |

EXAMPLE 2

Aqueous Formulations

The following Table II shows the components included in an aqueous formulation comprising BBI-4000, a soft anticholinergic ethyl ester, prepared and subjected to hydrolysis and stability testing:

TABLE II

| | Lot Number (% w/w) | | | | |
|---|---|---|---|---|---|
| Material | BB-61-1 | BB-62-1 | BB-63-1 | BB-64-1 | BB-65-1 |
| BBI-4000 | 2.00 | 2.00 | 2.00 | 2.00 | 2.00 |
| Hydroxyethyl Cellulose | 1.00 | 1.00 | 1.00 | 1.00 | 1.00 |
| Hexylene Glycol | 5.00 | 5.00 | 5.00 | 5.00 | 5.00 |
| Benzyl Alcohol | 1.00 | 1.00 | 1.00 | 1.00 | 1.00 |
| Ethanol 95% | 26.31 | 26.32 | 26.32 | 26.32 | 26.32 |
| Polysorbate 80 | 1.00 | 1.00 | 1.00 | 1.00 | 1.00 |
| Dimethiconol Blend 20 | 2.50 | 2.50 | 2.50 | 2.50 | 2.50 |
| Dibasic Sodium Phosphate, Dried | | 0.09 | 0.09 | 0.09 | |
| Monobasic Sodium Phosphate, Anhydrous | | 0.53 | 0.53 | 0.53 | |
| Citric Acid, Anhydrous | | | | | 0.20 |
| Trisodium Citrate Dihydrate | | | | | 1.16 |
| Water | 61.19 | 60.56 | 60.56 | 60.56 | 59.83 |
| 2N HCl | to pH 5 | to pH 4.5 | to pH 5 | to pH 5.5 | to pH 5 |
| 2N NaOH | to pH 5 | to pH 4.5 | to pH 5 | to pH 5.5 | to pH 5 |

An HPLC method was developed at a commercial laboratory for assaying the soft anticholinergic analog, and related substances (including hydrolysis products):

Apparatus

High performance liquid chromatography (HPLC) system
  Chromatography data system XBridge Shield RP18,4.6×150 mm, 3.5 µm HPLC column
Analytical balance capable of weighing to 0.00001 g
Ultrasonic bath
Volumetric flasks, 1, 5 mL
Syringe Filter: 25 mm, 0.45 µm, HPF Millex-HV, Millipore or suitable alternative
Reagents, Supplies, Media and Solutions:
BBI-4000 standard
Water, HPLC grade
Acetonitrile (can), Optima grade
Trifluroacetic acid (TFA), Fisher
Mobile Phase "A": 0.1% TFA in Water
Mobile Phase "B": 0.1% TFA in Acetonitrile
Auto Sampler Flush: 1:1 Water:Acetonitrile
Diluent: Acetonitrile
BBI-4000 Standard Preparation (2 mg/mL in Diluent):

The standards were prepared in duplicate by weighing 2.0±0.1 mg of BBI-4000 into 1 mL volumetric flasks. Dissolved and diluted to volume with acetonitrile and mixed by inversion.

Sample Preparation (BBI-4000 Gels):

Gel samples were prepared in duplicate at a target concentration of 2 mg/mL in a 5-mL volumetric flask. Added 1.5 ml $H_2O$ and mixed to disperse the sample. Diluted to volume with acetonitrile and filtered an aliquot through a syringe filter.

HPLC Conditions:

The liquid chromatographic system was set-up as follows:
HPLC Column: XBridge Shield RP18, 4.6×150 mm, 3.5 µm
Column Temp.: 25±1° C.
Sample Temp.: ambiant
Flow Rate: 1.5 mL/min
Injection Volume: 10 µL
UV Detection: 220 nm
Run Time: 20 minutes The HPLC assay was conducted on formulations at differing pH values, and the results were reviewed for "Time-Zero" and at 7 days at 40° C.:

The BBI-4000 content was determined. By Day 7, the assay number decreased, indicating hydrolysis of the BBI-4000 and some hydrolytic degradation products were noticeably increased (the two zwitterion stereoisomers, identified by RRT 0.84 and RRT 0.80), indicating lack of stability of this formulation system. Adjustment of pH, by itself, although providing a lower percent of hydrolytic degradation in the buffered formulation, did not resolve the issue.

A second experiment was conducted using a preparation comprising 2% of a soft glycopyrrolate ethyl ester (SGE) in an aqueous buffer system, which was tested for stability at refrigerated, 25° C. (RT), and 40° C., for 7 days, and showed the same trend or similar results.

Thus, independent of pH, when water or aqueous buffer is present, the SGE is relatively rapidly degraded by hydrolysis and is substantially reduced in less than one week.

EXAMPLE 3

Anhydrous Formulations

For preparing an anhydrous formulation, it is noted that no water or aqueous solution is added to the preparation.

The anhydrous formulations are based on: ethanol (solvent), hexylene glycol (moisturizer), and hydroxypropyl cellulose (HPC, gelling agent), in varying amounts or ratios. Each formulation was given an identification number as follows:

69-1=without antioxidant
73-2=without antioxidant but with polysorbate 80
72-2=adding propylene glycol and polysorbate 80
78-1 and 78-2=different quantities of HPC
79-1=with ascorbic acid as antioxidant/acidifying agent
79-2=with Vitamin E as antioxidant
84-1=with citric acid as antioxidant/acidifying agent Repeat-dose Studies up to 14 Days A 14-day dermal and systemic toxicity and toxicokinetics study in Göttingen Minipigs was conducted and completed using a formulation based on Formulations 79-1 and 84-1, above, but having a relatively high concentration of the active drug for testing tolerability. Specifically, the composition of the preparation used in this study included BBI-4000 as active ingredient (except in the vehicle-only control), hydroxypropyl cellulose as a gelling agent, hexylene glycol as an emollient, ascorbic acid or citric acid as antioxidant/pH adjuster and ethanol as the anhydrous vehicle.

Three groups of one male and one female animal were included in the main study, Group 1 receiving vehicle, Group 2 receiving BBI-4000 gel at 10% concentration and Group 3 receiving BBI-4000 gel at 20% concentration. All groups received 2 mL of gel formulation, once a day, for 14 consecutive days, applied to approximately 10% of their body surface area on their backs.

The study included daily observations of the site of application and scoring of erythema and edema (if present), daily general examinations including heart rate as well as pupil size assessment at days 1, 2, 3, 5, 7, 10 and 14. The frequent observations of heart rate and pupil size were intended to identify any potential systemic anticholinergic effect. Main organs were evaluated during necropsy and histopathology evaluation was completed for treated and untreated skin. Blood samples for chemistry and hematology analysis were collected as well as PK samples.

The results indicated that the composition was well-tolerated, there was no evidence of erythema or edema in the treated skin of any of the animals. Daily observation did not report any abnormality in heart rate or any other parameter. Pupil size assessments were reported as normal at all times in all animals. Blood chemistry and hematology parameters were reported within normal ranges. The necropsy did not reveal any abnormalities in any of the animals.

Histopathology analysis for the skin treated with an anhydrous composition comprising BBI-4000 was unremarkable and identical to non-treated and vehicle treated skin. All skin samples from the different groups were similar, with minor nonspecific changes that do not appear to be related to treatment. Mild, superficial inflammation reported in the dermis of most skin samples from all groups and from the non-treated areas suggests this finding is not drug or composition related, but associated with the caging of the animals.

The estimated BBI-4000 dose applied to the skin in this study was 40 mg/kg/day for Group 3 and 20 mg/kg/day for Group 2.

The PK analysis revealed variable, dose related systemic exposure of BBI-4000. The highest concentration was observed at 2 hours after Day-14 dosing in a minipig receiving the 20% BBI-4000 concentration. Most of the PK values for the carboxylic acid metabolite were below the lowest limit of quantification (LLOQ=4.75 ng/mL for this assay), consistent with the short half-life of this metabolite. Group 1 (vehicle) did not report any value above the LLOQ, as expected.

It was noted during the study that a reddish formulation residue was observed in the skin of all animals receiving the ascorbic acid-containing formulation. Although the residue could be removed with wiping from the skin, this type of residue would not be acceptable to a human subject; therefore, additional formulations were evaluated. A new experiment was conducted in 2 new pigs with a new formulation removing the ascorbic acid, adding citric acid instead. Testing of the citric acid-containing formulation was also well tolerated and no reddish or pink-colored residue was observed.

The following formulations, shown in Table III, were tested for stability:

TABLE III

| Component | A 84-1 % (w/w) | B 84-2 % (w/w) | C 84-3 % (w/w) |
|---|---|---|---|
| BBI-4000 | 10 | 10 | 10 |
| KLUCEL™ MF (Hydroxypropyl Cellulose) | 1.25 | 1.25 | 1.25 |
| Hexylene Glycol | 10 | 10 | 10 |
| DIMETHICONOL BLEND 20 | 2.5 | 2.5 | 2.5 |
| BHT | — | 0.1 | — |
| Propyl Gallate | — | — | 0.05 |
| Citric Acid, Anhydrous | 0.1 | 0.1 | 0.1 |
| Ethanol (200 proof) (Anhydrous Ethanol) | 76.15 | 76.05 | 76.1 |

KLUCEL™ MF hydroxylpropyl cellulose (HPC) is available commercially from a variety of sources. DOW CORNING® DIMETHICONOL BLEND 20 is a unique blend of silicone gum (6%) in dimethicone. BHT is butylated hydroxytoluene also known as dibutylhydroxytoluene.

BBI-4000 and non-BBI-4000 levels determined at time "zero" are shown in Table IV, below:

TABLE IV

| Day 0 Results | | BB-84-1 | | BB-84-2 | | BB-84-3 | |
|---|---|---|---|---|---|---|---|
| BBI-4000 | Assay (Wt %) | 9.81% | | 9.89% | | 9.72% | |
| | TAN % | 98.19% | | 95.15% | | 92.17% | |
| | | RRT | Area % | RRT | Area % | RRT | Area % |
| Non-BBI-4000 by HPLC (%) | | RRT 0.80 | 0.67% | | | | |
| | | RRT 0.96 | 0.10% | RRT 0.80 | 0.62% | RRT 0.64 | 6.07% |
| | | RRT 1.09 | 0.86% | RRT 0.96 | 0.07% | RRT 0.80 | 0.69% |
| | | RRT 1.48 | 0.19% | RRT 1.09 | 0.79% | RRT 0.96 | 0.09% |
| | | | | RRT 1.49 | 0.16% | RRT 1.09 | 0.81% |
| | | | | RRT 2.05 | 0.90% | RRT 1.49 | 0.17% |
| | | | | RRT 2.07 | 2.31% | | |
| Total Non-BBI-4000 by HPLC | | 1.82% | | 4.85% | | 7.83% | |

BBI-4000 and non-BBI-4000 levels determined at 7 days, under accelerated conditions, 40° C., are shown in Table V, below:

TABLE V

| Day 7 Results | | BB-84-1 | | BB-84-2 | | BB-84-3 | |
|---|---|---|---|---|---|---|---|
| BBI-4000 | Assay (Wt %) | 10.32% | | 10.18% | | 10.08% | |
| | TAN % | 97.89% | | 94.75% | | 93.84% | |
| | | RRT | Area % | RRT | Area % | RRT | Area % |
| Non-BBI-4000 by HPLC (%) | | RRT 0.80 | 0.59% | RRT 0.80 | 0.42% | RRT 0.64 | 4.28% |
| | | RRT 0.82 | 0.03% | RRT 0.91 | 0.16% | | |
| | | RRT 0.91 | 0.17% | RRT 0.96 | 0.15% | RRT 0.80 | 0.58% |
| | | RRT 0.96 | 0.29% | RRT 1.09 | 0.96% | RRT 0.96 | 0.20% |
| | | RRT 1.08 | 0.04% | RRT 1.49 | 0.18% | RRT 1.09 | 0.90% |
| | | RRT 1.09 | 0.80% | RRT 1.50 | 0.02% | RRT 1.49 | 0.18% |
| | | RRT 1.49 | 0.19% | RRT 2.05 | 0.88% | RRT 1.50 | 0.02% |
| | | RRT 1.50 | 0.01% | RRT 2.07 | 2.49% | | |
| Total Non-BBI-4000 by HPLC (%) | | 2.11% | | 5.25% | | 6.16% | |

All formulations showed good stability, however fewer non-BBI-4000 materials were identified in formulations where antioxidants propyl gallate or BHT were absent from the formulation.

Further stability testing has been completed for a 3-month time-frame, using Formulation No. 84-1, tested at three temperatures: accelerated (40° C.), room temperature (25° C.), and refrigerated (about 4° C.). Formulation No. 84-1 was specifically prepared using the following preparation instructions:

a) Combine the hexylene glycol and ethanol in a suitable container and mix.

b) Add the citric acid and stir to dissolve.

c) Add the active (BBI-4000) and stir to dissolve.

d) Add the KLUCEL™ MF and stir to dissolve, to increase viscosity of the product.

e) Lastly, add the DIMETHICONOL BLEND 20 and briefly disperse.

f) Homogenize the mixture of steps a) through e). For small batches, homogenation can be carried out by passing/mixing between 2 syringes connected with a micro-emulsifying needle. For larger batches, an overhead or inline homogenizer may be required.

The results of the 3-month stability study are provided in Table VI, below:

TABLE VI

Stability of Formulation A 84-1

| Day/<br>Temperature | 0 | 7 D-<br>40° C. | 14 D-<br>40° C. | 30 D-<br>40° C. | 30 D-<br>5° C. | 90 D-<br>5° C. | 30 D-<br>25° C. | 90 D-<br>25° C. |
|---|---|---|---|---|---|---|---|---|
| Assay BBI-4000 (%) | 9.81 | 10.32 | 10.21 | 10.25 | 9.32 | 10.50 | 10.26 | 10.63 |
| Total Non-BBI-4000 by HPLC (%) | 1.82 | 2.12 | 2.12 | 3.48 | 2.77 | 2.35 | 3.29 | 3.87 |

The formulation 84-1, having the formulation shown in Table VII, showed good stability and was tested in vivo.

TABLE VII

| Component | A 84-1<br>% (w/w) |
|---|---|
| BBI-4000 | 10 |
| KLUCEL ™ MF<br>(Hydoxypropyl Cellulose) | 1.25 |
| Hexylene Glycol | 10 |
| DIMETHICONOL BLEND 20 | 2.5 |
| Citric Acid, Anhydrous | 0.1 |
| Ethanol (200 proof)<br>(Anhydrous Ethanol) | 76.15 |

In the following clinical study, the A 84-1 formulation above was modified slightly. For 5% and 10% BBI-4000 gels, respectively, 0.001% anhydrous citric acid was used and the amount of ethanol adjusted accordingly (81.25% for the 5% gel and 76.25% for the 10% gel).

EXAMPLE 4

Clinical Study

Study BBI-4000-CL-101: A Single-Center, Randomized, Double-Blind, Vehicle Controlled Study to Evaluate the Safety and the Effect on Sweat Production of Topically Applied BBI-4000 Gel in Subjects with Hyperhidrosis Study Design and Inclusion Criteria Study BBI-4000-CL-101 was a Phase 1, randomized, double-blind, vehicle-controlled study of BBI-4000 gel conducted in 24 subjects with axillary hyperhidrosis. The study was conducted at a single center in the Dominican Republic. This study was not conducted under a US IND, but was undertaken in full compliance with applicable regulations of the Dominican Republic and with good clinical practice guidelines.

The objectives of this exploratory study were to evaluate the safety, local tolerability, and the effects on sweat production of topically applied BBI-4000 gel. A preliminary assessment of systemic exposure based on the pharmacokinetics of BBI-4000 was also conducted following topical application of the gel.

The drug product used in this study was an anhydrous semi-transparent gel with a composition including BBI-4000, hydroxypropylcellulose, hexylene glycol, DIMETHICONOL BLEND 20, citric acid, and ethanol.

The study consisted of 2 consecutive cohorts, where Cohort 1 established acceptable tolerability of 5% BBI-4000 gel (applied to one axilla) prior to enrolling a separate group of subjects into Cohort 2:

Cohort 1: 6 subjects received 5% BBI-4000 gel in one axilla and vehicle in the other once daily (at night) for 14 consecutive days, based on a randomized, split-body design.

Cohort 2: 18 subjects (6 in each treatment group) were randomized to receive 5% BBI-4000 gel, 10% BBI-4000 gel, or vehicle (control) to both axillae once daily (at night) for 14 consecutive days, based on a parallel-group design.

Subjects were 18 to 45 years of age, in good general health, with a diagnosis of primary axillary hyperhidrosis based on the following criteria at baseline:

HDSS of 3 or 4 (HDSS=Hyperhidrosis Disease Severity Score)

Gravimetric test indicating at least an average of 100 mg of sweat production in each axilla in 5 minutes at rest (at 25° C. to 27° C.)

Bilateral and symmetrical hyperhidrosis

Subjects with prior axillary use of botulinum toxin (within 2 years) or receiving any anticholinergic medication were not eligible to participate in the study. All female subjects of child-bearing potential were required to use a medically acceptable method of contraception while on active treatment.

Subjects were not allowed to use any antiperspirant 7 days prior to baseline assessments and for the duration of the study.

Study Assessments and Endpoints

Assessment of Local Tolerability

Local tolerability to topical BBI-4000 was assessed by the investigator (erythema, dryness, and scaling) and study subjects (burning and itching).

The investigator graded the severity of erythema, dryness, and scaling for each axilla based on a 4-point scale, where "0" was absent, "1" was minimal (barely perceptible), "2" was mild, "3" was moderate, and "4" was severe.

Subjects graded the severity of any burning or itching based on a 4-point scale, where "0" was absent, "1" was minimal (an awareness, but no discomfort), "2" was mild, "3" was moderate, and "4" was severe.

Assessment of Safety

Safety was assessed by AEs, serious AEs (SAEs), or unexpected AEs; vital signs (blood pressure and heart rate); and clinical laboratory measures (hematology, chemistry, and urinalysis). Clinically relevant laboratory findings were to be collected as AEs (AEs=adverse events).

Assessment of Efficacy

Efficacy was assessed by the change in gravimetrically measured sweat production and the change in hyperhidrosis disease severity scale (HDSS) from baseline to Day 15 (end of therapy).

For the gravimetric assessment, sweat production was measured by placing filter paper (pre-weighed) on the axilla for 5 minutes while the subject was in a semi-reclining position at room temperature. The filter paper was covered with plastic during exposure to the axilla, and was then weighed following the 5-minute exposure period to calculate the amount of sweat produced.

For the HDSS, subjects rated the severity of their hyperhidrosis on a 4-point scale (1, 2, 3, or 4) based on the level of interference with their daily activities. A score of 1 indicated that "my sweating is never noticeable and never interferes with my daily activities" and a score of 4 indicated that "my sweating is intolerable and always interferes with my daily activities".

Key Results of Study BBI-4000-CL-101

All subjects completed the study, including the follow-up visit at Day 16, and received 14 days of study treatment in accordance with the study protocol. All subjects were included in the analysis of study assessments (evaluable population). The subjects in Cohort 1 (split-body) had no AEs reported and tolerated well the 5% BBI-4000 gel and vehicle with only minimal to mild dryness and erythema reported in a couple of subjects during the study.

The results from Cohort 2 subjects, who received study drug in both axillary areas in a parallel design, are considered the most informative data from this study and are the focus of the following sections.

This was an exploratory study not powered to achieve statistically significant differences in the efficacy parameters measured, but to provide an early indication of safety, tolerability, and the potential treatment effect of topically applied BBI-4000.

Baseline Demographics and Disease Characteristics

Subjects in Cohort 2 ranged from 18.6 to 43.7 years of age, with a median age of ≤31 years in each treatment group. All subjects were Hispanic/Latino. No imbalances were noted between treatment groups with regard to gender, race, or ethnicity.

Measures of sweat production at baseline were generally similar between treatment groups and consistent with axillary hyperhidrosis. Median sweat production was >200 mg (both axillae) in a 5-minute period for all treatment groups based on baseline gravimetric assessment. All subjects had an HDSS score of 3 or 4 at baseline.

Local Tolerability

Investigator and subject-based assessments of local tolerability indicated that 5% and 10% BBI-4000 gel topically applied to the axilla region was well tolerated over the 14-day treatment period. Dryness, erythema, itching and burning were occassionally reported by 1 or 2 subjects, they were minimal and did not lead to discontinuation of the therapy in any individual.

Safety

No AEs were reported by any subjects during the conduct of the study, and no deaths or serious AEs were reported.

There were no changes in laboratory parameters that were considered clinically relevant through the follow-up period (Day 16), as indicated by no reports of laboratory-related AEs by the investigator.

There were no clinically relevant changes from baseline in vital signs (blood pressure and heart rate) for any treatment group in either cohort during the study.

Efficacy

BBI-4000 formulation showed achievement of a greater reduction in gravimetrically measured sweat production and a greater improvement in HDSS assessments, when compared to vehicle. Although the overall reduction in sweat production and the HDSS improvement endpoints suggest than BBI-4000 10% gel performed better than BBI-4000 5% gel, it is difficult to make a definitive conclusion regarding differences in the magnitude of effect of the 2 active arms with this small sample size. Results for the key endpoints that have been commonly associated with a clinically meaningful improvement (i.e., reduction in sweat product of at least 50% and ≥2-point improvement in HDSS) are here provided for the aggregate number of subjects exposed to BBI-4000 in comparison to vehicle.

The proportion of subjects treated with BBI-4000 who had at least a 50% reduction in sweat production at Day 15 was 75% (9 of 12) compared with 33% (2 of 6) of subjects who received vehicle. In addition 8 of 12 (67%) subjects receiving BBI-4000 reported a 2-point improvement in HDSS at Day 15, compared with 2 of 6 (33%) in the vehicle group. This reduction in HDSS score represents a meaningful change from intolerable or barely tolerable hyperhidrosis to tolerable or never noticeable hyperhidrosis for these subjects.

EXAMPLE 5

Further Anhydrous Formulations

Other formulations were developed, as set forth in the following table.

TABLE VIII

| Component | Composition (% w/w) | | | | |
| --- | --- | --- | --- | --- | --- |
| | Gel 2 | Gel 3 | Gel 4 | Gel 5 | Gel 6 |
| Hydropropyl Cellulose | 1.250 | 1.250 | 1.250 | 1.250 | 1.250 |
| BBI-4000 | 5.000 | 5.000 | 5.000 | 5.000 | 5.000 |
| Hexylene Glycol | 10.000 | 10.000 | 10.000 | 10.000 | 10.000 |
| Citric Acid, Anhydrous | 0.001 | 0.001 | 0.001 | 0.001 | 0.001 |
| Talc | 0.500 | — | — | — | — |
| C12-15 Alkyl Lactate | — | 2.500 | — | — | — |
| Dimethicone copolyol | — | — | 1.000 | — | — |
| Magnesium stearate | — | — | — | 0.001 | — |
| Isopropyl myristate (IPM) | — | — | — | — | 2.500 |
| Ethanol, Anhydrous | qs to 100 | qs to 100 | qs to 100 | qs to 100 | qs to 100 |
| Visual appearance at t = 0 | Translucent, med-high viscosity, smooth | Clear colorless, low viscosity, smooth | Clear colorless, low viscosity, smooth | Clear colorless, low viscosity, smooth | Clear colorless, low viscosity, smooth |
| Assessed for short-term stability | √ | √ | √ | √ | √ |

By way of example, the amount of BBI-4000 can alternatively be 10.000, 15.000 or 20.000 (% w/w), with the quantity of anhydrous ethanol adjusted accordingly.

Other formulations in accord herewith are listed in Table IX below.

TABLE IX

| Component | Composition (% w/w) | | | | |
| --- | --- | --- | --- | --- | --- |
| | Gel AA | Get BB | Gel CC | Gel DD | Gel EE |
| Hydropropyl Cellulose | 1.250 | 1.250 | 1.250 | 1.250 | 1.250 |
| BBI-4000 | 10.000 | 10.000 | 10.000 | 10.000 | 10.000 |
| Hexylene Glycol | 10.000 | 10.000 | 10.000 | 10.000 | 10.000 |

TABLE IX-continued

| Component | Composition (% w/w) | | | | |
|---|---|---|---|---|---|
| | Gel AA | Get BB | Gel CC | Gel DD | Gel EE |
| Citric Acid, Anhydrous | 0.001 | 0.001 | 0.001 | 0.001 | 0.001 |
| Dimethicone, e.g. 350 cSt | 1.000 | 0.500 | — | 1.000 | 1.000 |
| Cyclomethicone, e.g. 5-NF | 1.000 | 1.000 | 1.000 | — | — |
| Isopropyl myristate | — | — | 2.500 | — | 2.500 |
| Myristyl propionate | — | — | — | 2.500 | — |
| Ethanol, Anhydrous | qs to 100 | qs to 100 | qs to 100 | qs to 100 | qs to 100 |

By way of example, the amount of BBI-4000 can alternatively be 5.000% w/w, 15.000% w/w or 20.000% w/w, with the amount of anhydrous ethanol adjusted accordingly.

The following is a general formulation for particularly preferred embodiments of the subject composition.

Formulation

| Component | Amount |
|---|---|
| BBI-4000 | 1% to 20% w/w |
| Hexylene Glycol | 10% w/w |
| Hydroxypropyl Cellulose | 1.25% w/w |
| Citric Acid, Anhydrous | 0.001% w/w |
| Dimethiconol Blend 20 or Isopropyl Myristate | 2.5% w/w |
| Anhydrous Ethanol | qs to 100% w/w |

Additional preferred embodiments include dimethicone or cyclomethicone, separately or in combination, in place of Dimethiconol Blend 20, optionally together with isopropyl myristate, in the above formulation.

In these compositions, isopropyl myristate is preferred over Dimethiconol Blend 20 for two reasons. The first reason is related to transfer and scale-up of manufacturing process. It has been found difficult to stabilize the droplets of Dimethiconol Blend 20 in the formulation when attempting to increase the batch size and transfer the manufacturing process. Over time, a small amount of Dimethiconol Blend 20 coalesces at the bottom of the container in small droplets. The change to isopropyl myristate (IPM) eliminates this. The second reason is related to FDA acceptance of Dimethiconol Blend 20. While Dimethiconol Blend 20 is an acceptable ingredient in cosmetic preparations, it has not been previously approved in pharmaceutical formulations. The FDA accepted its use in clinical studies, but additional studies might be needed to qualify it in a final formulation. The change to isopropyl myristate eliminates the need to conduct this additional testing as IPM has been approved in other pharmaceutical preparations, Dimethiconol Blend 20 was not detrimental to the function of the formulation; however, isopropyl myristate provides benefits to scale-up and commercialization. After evaluating a number of alternatives, isopropyl myristate was selected based upon its ability to reduce tack during drying as well as provide similar in vitro permeability. It also provided a formulation with a similar chemical stability profile to Dimethiconol Blend 20. The isopropyl myristate formulation was compared to the Dimethiconol Blend 20 formulation in a preclinical animal study. The isopropyl myristate formulation demonstrated an increase in permeation in mini-pigs relative to the Dimethiconol Blend 20 formulation. Two upcoming studies in humans are planned. The first study will compare the pharmacokinetics of 5% and 15% BBI-4000 gels containing isopropyl myristate with 15% BBI-4000 gel containing Dimethiconol Blend 20. The second study will evaluate/confirm the efficacy of BBI-4000 gel containing isopropyl myristate.

While certain preferred and alternative embodiments have been set forth for purposes of disclosure, modifications to the disclosed embodiments may occur to those who are skilled in the art. Accordingly, this specification is intended to cover all embodiments and combinations and modifications thereof which do not depart from the spirit and scope of the following claims.

What we claim is:

1. An anhydrous topical gel composition comprising:
   (a) a compound having the formula:

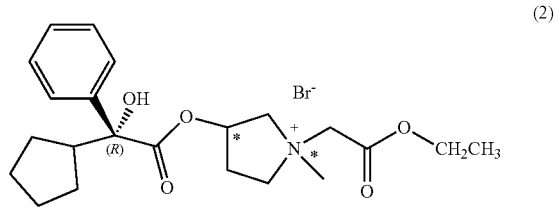

(2)

said compound having the R stereoisomeric configuration at the 2 position and the R, S or RS stereoisomeric configuration at the 1' and 3' positions, or being a mixture thereof;
   (b) anhydrous ethanol;
   (c) at least one gelling or viscosity-controlling ingredient comprising hydroxypropyl cellulose;
   (d) citric acid;
   (e) hexylene glycol;
   (f) isopropyl myristate; and
   (g) optionally, at least one additional carrier or excipient provided that said anhydrous topical gel composition is anhydrous and comprises from about 1% to about 25% w/v or w/w of the compound of formula (2), said anhydrous topical gel composition having greater storage stability compared to a composition comprising an aqueous solvent or aqueous buffer, with the proviso that said ingredients are present in amounts such that the product of any transesterification is the same as the compound of formula (2), and/or with the proviso that said anhydrous ethanol is present in an amount sufficient to act as a non-aqueous solvent for the compound of formula (2).

2. The anhydrous topical gel composition of claim 1, wherein the anhydrous topical gel composition comprises at least about 70% w/w anhydrous ethanol.

3. The anhydrous topical gel composition of claim 2, wherein the anhydrous topical gel composition comprises from about 70% to about 99.99% w/w anhydrous ethanol.

4. The anhydrous topical gel composition of claim 3, wherein the anhydrous topical gel composition comprises from about 70% to about 85% w/w anhydrous ethanol.

5. The anhydrous topical gel composition of claim 1, wherein the anhydrous topical gel composition comprises at least one additional carrier or excipient.

6. The anhydrous topical gel composition of claim 1, wherein the compound of formula (2) is selected from the group consisting of:

(i) 3-(2-cyclopentyl-2-phenyl-2-hydroxyacetoxy)-1-(ethoxycarbonylmethyl)-1-methylpyrrolidinium bromide;
(ii) (2R) 3-(2-cyclopentyl-2-phenyl-2-hydroxyacetoxy)-1-(ethoxycarbonylmethyl)-1-methylpyrrolidinium bromide;
(iii) (2R,3'R) 3-(2-cyclopentyl-2-phenyl-2-hydroxyacetoxy)-1-(ethoxycarbonylmethyl)-1-methylpyrrolidinium bromide;
(iv) (2R,3'S) 3-(2-cyclopentyl-2-phenyl-2-hydroxyacetoxy)-1-(ethoxycarbonylmethyl)-1-methylpyrrolidinium bromide;
(v) (2R,1'R,3'S) 3-(2-cyclopentyl-2-phenyl-2-hydroxyacetoxy)-1-(ethoxycarbonylmethyl)-1-methylpyrrolidinium bromide;
(vi) (2R,1'S,3'S) 3-(2-cyclopentyl-2-phenyl-2-hydroxyacetoxy)-1-(ethoxycarbonylmethyl)-1-methylpyrrolidinium bromide;
(vii) (2R,1'R,3'R) 3-(2-cyclopentyl-2-phenyl-2-hydroxyacetoxy)-1-(ethoxycarbonylmethyl)-1-methylpyrrolidinium bromide; and
(viii) (2R,1'S,3'R) 3-(2-cyclopentyl-2-phenyl-2-hydroxyacetoxy)-1-(ethoxycarbonylmethyl)-1-methylpyrrolidinium bromide.

7. The anhydrous topical gel composition of claim 1, wherein the anhydrous topical gel composition comprises the compound of formula (2) at a concentration of from about 1% w/v or w/w to about 20% w/v or w/w.

8. The anhydrous topical gel composition of claim 7, wherein the anhydrous topical gel composition comprises the compound of formula (2) at a concentration of from about 2% w/v or w/w to about 10% w/v or w/w.

9. The anhydrous topical gel composition of claim 8, wherein the anhydrous topical gel composition is packaged in a multiple dose container that meters a dose of from about 0.5 ml to about 1.0 ml of the composition for each application.

10. The anhydrous topical gel composition of claim 1, wherein the anhydrous topical gel composition is packaged in a single or unit dose container that delivers a single or unit dose of about 0.5 ml to about 1.0 ml of the composition for each application.

11. The anhydrous topical gel composition of claim 1, wherein the anhydrous topical gel composition further comprises at least one member selected from the group consisting of dimethicone and cyclomethicone.

12. The anhydrous topical gel composition of claim 1, wherein the anhydrous topical gel composition further comprises a 6% silicone gum blend in dimethicone.

13. The anhydrous topical gel composition of claim 1, wherein said anhydrous topical gel composition is topically administered to an affected skin area of the subject, within 1-2 hours prior to the subject's sleep period.

14. The anhydrous topical gel composition of claim 1, wherein said anhydrous topical gel composition is topically administered in a one to four times daily regimen to an affected skin area of a subject.

15. A method of treating hyperhidrosis in a subject, said method comprising topically administering an anhydrous topical gel composition to skin of an area of a subject suffering from hyperhidrosis, before bedtime, such that, compared to untreated, baseline conditions, sweat production is reduced by at least 25% for at least six (6) hours; and such that sweat production is reduced by an amount substantially equivalent to an amount that sweat production is reduced as compared to untreated, baseline conditions, following administration of a composition comprising the same concentration of glycopyrrolate, and with an improved safety profile compared to topical glycopyrrolate,
wherein said anhydrous topical gel composition comprises the following ingredients:
(a) a compound having the formula:

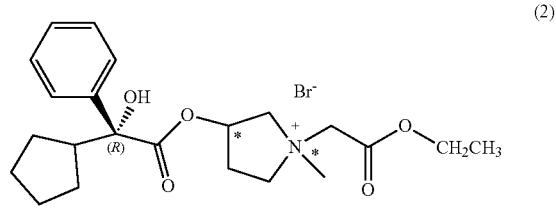

said compound having the R stereoisomeric configuration at the 2 position and the R, S or RS stereoisomeric configuration at the 1' and 3' positions, or being a mixture thereof;
(b) anhydrous ethanol;
(c) at least one gelling or viscosity-controlling ingredient comprising hydroxypropyl cellulose; and
(d) citric acid;
(e) hexylene glycol;
(f) isopropyl myristate; and
(g) optionally, at least one additional carrier or excipient
provided that said anhydrous topical gel composition is anhydrous and comprises from about 1% to about 25% w/v or w/w of the compound of formula (2), said anhydrous topical gel composition having greater storage stability compared to a composition comprising an aqueous solvent or aqueous buffer, with the proviso that said ingredients are present in amounts such that the product of any transesterification is the same as the compound of formula (2), and/or with the proviso that said anhydrous ethanol is present in an amount sufficient to act as a non-aqueous solvent for the compound of formula (2),
wherein the anhydrous topical gel composition is administered by application to an anatomic area selected from a hand palm area, a foot plantar area, a groin area, an axilla area, and a facial area of the subject.

16. The method of claim 15, wherein the anhydrous topical gel composition comprises at least about 70% w/w anhydrous ethanol.

17. The method of claim 16, wherein the anhydrous topical gel composition comprises from about 70% to about 99.99% w/w anhydrous ethanol.

18. The method of claim 17, wherein the anhydrous topical gel composition comprises from about 70% to about 85% w/w anhydrous ethanol.

19. The method of claim 15, wherein the anhydrous topical gel composition comprises at least one additional carrier or excipient.

20. The method of claim 15, wherein the compound of formula (2) is selected from the group consisting of:
(i) 3-(2-cyclopentyl-2-phenyl-2-hydroxyacetoxy)-1-(ethoxycarbonylmethyl)-1-methylpyrrolidinium bromide;
(ii) (2R) 3-(2-cyclopentyl-2-phenyl-2-hydroxyacetoxy)-1-(ethoxycarbonylmethyl)-1-methylpyrrolidinium bromide;
(iii) (2R,3'R) 3-(2-cyclopentyl-2-phenyl-2-hydroxyacetoxy)-1-(ethoxycarbonylmethyl)-1-methylpyrrolidinium bromide;

(iv) (2R,3'S) 3-(2-cyclopentyl-2-phenyl-2-hydroxyacetoxy)-1-(ethoxycarbonylmethyl)-1-methylpyrrolidinium bromide;

(v) (2R,1'R,3'S) 3-(2-cyclopentyl-2-phenyl-2-hydroxyacetoxy)-1-(ethoxycarbonylmethyl)-1-methylpyrrolidinium bromide;

(vi) (2R,1'S,3'S) 3-(2-cyclopentyl-2-phenyl-2-hydroxyacetoxy)-1-(ethoxycarbonylmethyl)-1-methylpyrrolidinium bromide;

(vii) (2R,1'R,3'R) 3-(2-cyclopentyl-2-phenyl-2-hydroxyacetoxy)-1-(ethoxycarbonylmethyl)-1-methylpyrrolidinium bromide; and (viii) (2R,1'S,3'R) 3-(2-cyclopentyl-2-phenyl-2-hydroxyacetoxy)-1-(ethoxycarbonylmethyl)-1-methylpyrrolidinium bromide.

21. The method of claim 15, wherein the anhydrous topical gel composition comprises the compound of formula (2) at a concentration of from about 1% w/v or w/w to about 20% w/v or w/w.

22. The method of claim 21, wherein the anhydrous topical gel composition comprises the compound of formula (2) at a concentration of from about 2% w/v or w/w to about 10% w/v or w/w.

23. The method of claim 15, wherein the anhydrous topical gel composition is packaged in a multiple dose container that meters a dose of from about 0.5 ml to about 1.0 ml of the composition for each application.

24. The method of claim 15, wherein the anhydrous topical gel composition is packaged in a single or unit dose container that delivers a single or unit dose of about 0.5 ml to about 1.0 ml of the composition for each application.

25. The method of claim 15, wherein the compound of formula (2) is (2R, 3'R) 3-(2-cyclopentyl-2-phenyl-2-hydroxyacetoxy)-1-(ethoxycarbonylmethyl)-1-methylpyrrolidinium bromide.

26. The method of claim 15, wherein the anhydrous topical gel composition further comprises at least one member selected from the group consisting of dimethicone and cyclomethicone.

27. The method of claim 15, wherein the anhydrous topical gel composition further comprises a 6% silicone gum blend in dimethicone.

28. The method of claim 15, wherein said anhydrous topical gel composition is topically administered to an affected skin area of the subject, within 1-2 hours prior to the subject's sleep period.

29. The method of claim 15, wherein said anhydrous topical gel composition is topically administered in a one to four times daily regimen to an affected skin area of a subject.

* * * * *